United States Patent
Dhurandhar et al.

(10) Patent No.: US 9,433,659 B2
(45) Date of Patent: Sep. 6, 2016

(54) ENHANCED GLYCEMIC CONTROL USING AD36E4ORF1 AND AKT1 INHIBITOR

(71) Applicant: BOARD OF SUPERVISORS OF LOUISIANA ST. UNIV. & AGRICULTURAL & MECHANICAL COLLEGE, Baton Rouge, LA (US)

(72) Inventors: Nikhil Dhurandhar, Baton Rouge, LA (US); Rashmi Krishnapuram, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 14/370,317

(22) PCT Filed: Jan. 18, 2013

(86) PCT No.: PCT/US2013/022126
§ 371 (c)(1),
(2) Date: Jul. 2, 2014

(87) PCT Pub. No.: WO2013/109876
PCT Pub. Date: Jul. 25, 2013

(65) Prior Publication Data
US 2015/0038412 A1 Feb. 5, 2015

Related U.S. Application Data

(60) Provisional application No. 61/588,959, filed on Jan. 20, 2012.

(51) Int. Cl.

| | |
|---|---|
| *A61K 38/16* | (2006.01) |
| *A61K 45/06* | (2006.01) |
| *A61K 31/145* | (2006.01) |
| *A61K 48/00* | (2006.01) |
| *A61P 3/10* | (2006.01) |
| *C07K 14/005* | (2006.01) |
| *A61K 31/433* | (2006.01) |

(52) U.S. Cl.
CPC ........... *A61K 38/162* (2013.01); *A61K 31/145* (2013.01); *A61K 31/433* (2013.01); *A61K 45/06* (2013.01); *C07K 14/005* (2013.01); *A61K 48/005* (2013.01); *C12N 2710/10322* (2013.01); *C12N 2710/10333* (2013.01)

(58) Field of Classification Search
None
See application file for complete search history.

(56) References Cited

U.S. PATENT DOCUMENTS

2009/0264356 A1* 10/2009 Dhurandhar et al. .......... 514/12

OTHER PUBLICATIONS

Dhurandhar, "The role of Ad-36 and its E4orf-1 protein in modulating glycemic control," dissertation, Louisiana State University and Agricultural and Mechanical College pp. 1-173 (Aug. 2011)—available at URL etd.lsu.edu/docs/available/etd-06082011-093407/.*
Dummler et al., "Physiological roles of PKB/Akt isoforms in development and disease," Biochem. Soc. Trans. 35:231-235 (2007).*
eMedicine Health, diabetes causes, http://www.onhealth.com/diabetes_health/page3.htm#diabetes_causes (referenced Aug. 22, 2013).*
United Healthcare, diabetes, http://www.uhc.com/source4women/health_topics/diabetes/relatedinformation/d0f0417b073bf110VgnVCM1000002f10b10a__.htm—referenced Aug. 22, 2013.*
Dyck et al., "The prevalence by staged severity of various types of diabetic neuropathy, retinopathy, and nephropathy in a population-based cohort: the Rochester diabetic neuropathy study," Neurol. 43:817-824 (1993).*
International Search Report from corresponding PCT Application No. PCT/US2013/022126 dated Jun. 10, 2013.
Dubuisson et al. "PPARγ-Independent Increase in Glucose Uptake and Adiponectin Abundance in Fat Cells," Endocrinology, 52:3648-3660 (2011).
Dhurandhar et al. "E4orf1: A Novel Ligand That Improves Glucose Disposal in Cell Culture," PLOS ONE 6:1-11 (2011).
Krishnapuram et al., "Template to Improve Glycemic Control Without Reducing Adiposity or Dietary Fat," Am. J. Physiol. Endocrinol. and Metab., 300:E779-E789 (2011).
Wan et al., "Loss of Akt1 in Mice Increases Energy Expenditure and Protects Against Diet-Induced Obesity" Molecular and Cellular Biology, 32:96-106 (2011).
Zeng et al., "2-Aminothiadiazole Inhibitors of AKT1 as Potential Cancer Therapeutics," Bioorganic and Medicinal Chemistry Letters, 20:1652-1656 (2010).

* cited by examiner

*Primary Examiner* — Julie Ha
*Assistant Examiner* — Kristina M Hellman
(74) *Attorney, Agent, or Firm* — McDermott Will & Emery LLP

(57) ABSTRACT

This invention generally relates to methods for improving glycemic control by administering an Ad36 composition and an AKT1 inhibitor.

6 Claims, 10 Drawing Sheets

SEQUENCE LISTING

<160> NUMBER OF SEQ ID NOS: 2

<210> SEQ ID NO 1
<211> LENGTH: 378
<212> TYPE: DNA
<213> ORGANISM: Human adenovirus

```
<400> SEQUENCE: 1
atggctgaat ctctgtatgc tttcatagat agccctggag ggatcgctcc cgtccaggaa       60
ggggctagca atagatatat cttcttttgc cccgaatctt tccacattcc tccgcatggg      120
gtgatattgc ttcacctcag agtgagcgtg ctggttccta ctggatatca gggcagattt      180
atggccttga tgactacca tgccaggggc atactaaccc agtccgatgt gatatttgcc       240
gggagaagac atgatctctc tgtgctgctc tttaaccaca cggaccgatt tttgtatgtc      300
cgcgagggcc acccagtggg aaccctgctg ctggagagag tgattttttcc ttcagtgaga    360 atagccaccc tggtttag                                                    378

<210> SEQ ID NO 2
<211> LENGTH: 125
<212> TYPE: PRT
<213> ORGANISM: Human adenovirus

<400> SEQUENCE: 2

Met Ala Glu Ser Leu Tyr Ala Phe Ile Asp Ser Pro Gly Gly Ile Ala
1               5                   10                  15

Pro Val Gln Glu Gly Ala Ser Asn Arg Tyr Ile Phe Phe Cys Pro Glu
            20                  25                  30

Ser Phe His Ile Pro Pro His Gly Val Ile Leu Leu His Leu Arg Val
        35                  40                  45

Ser Val Leu Val Pro Thr Gly Tyr Gln Gly Arg Phe Met Ala Leu Asn
    50                  55                  60

Asp Tyr His Ala Arg Gly Ile Leu Thr Gln Ser Asp Val Ile Phe Ala
65                  70                  75                  80

Gly Arg Arg His Asp Leu Ser Val Leu Leu Phe Asn His Thr Asp Arg
                85                  90                  95

Phe Leu Tyr Val Arg Glu Gly His Pro Val Gly Thr Leu Leu Leu Glu
            100                 105                 110

Arg Val Ile Phe Pro Ser Val Arg Ile Ala Thr Leu Val
            115                 120                 125
```

ENHANCED GLYCEMIC CONTROL USING AD36E4ORF1 AND AKT1 INHIBITOR

RELATED APPLICATIONS

This application is the U.S. National Stage of International Application No. PCT/US2013/022126, filed Jan. 18, 2013, published in English, which claims the benefit of U.S. Provisional Application No. 61/588,959, filed on Jan. 20, 2012, the entire teachings of these applications are incorporated herein by reference.

SEQUENCE LISTING

The instant application contains a Sequence Listing which has been submitted electronically in ASCII format and is hereby incorporated by reference in its entirety. Said ASCII copy, created on Jun. 11, 2014, is named 071176-0050_SL.txt and is 2,125 bytes in size.

BACKGROUND

The binding of insulin to its cell surface receptor initiates a cascade of cell signaling, which involves the activation of phosphatidyl inositol 3-kinase (PI3K) via the insulin receptor substrates (IRS) (FIG. 1). PI3K in turn activates the enzyme AKT, leading to the translocation of glucose transporters (Glut4) to cell surface. Glucose transporters bring glucose inside a cell. A defect in cellular uptake of glucose can lead to accumulation of glucose outside a cell (in circulation), leading to a hyperglycemic or diabetic state. In contrast, increasing cellular glucose uptake can clear it from the circulation, thus improving hyperglycemia or diabetes.

Ad36 is a human adenovirus that increases adiposity in experimentally infected animals, yet improves their glycemic control (1, 2). In humans, natural infection with Ad36 is associated with better glycemic control (1). Cell signaling studies have shown that Ad36 up-regulates PI3K activation, not via the conventional insulin-IRS pathway, but instead via activating Ras (FIG. 1), which leads to enhanced uptake of glucose in adipocytes and myocytes (3-5). In adipocytes and their progenitors, Ad36 up-regulates PPARγ, a key gene that initiates adipogenesis, which leads to a greater differentiation of fat cells, and lipid accumulation, and consequentially, greater adiposity (6, 7). On the other hand, Ad36 increases glucose uptake in adipose tissue and adipocytes (8). Thus, Ad36 possesses the dual property of increasing adiposity, yet improving glycemic control.

The adipogenic and glycemic effects of Ad36 are mediated via its E4orf1 protein, which up-regulates PPARγ, increases adiposity and increases cellular glucose uptake (9, 10). Up-regulation of PPARγ is also associated with improved glycemic control. The thiazolidinedione (TZD) class of anti-diabetic drugs up-regulate PPARγ and improve glycemic control, while also increasing adiposity (11, 12). The dual action of Ad36 or its E4orf1 protein is similar to that of the thiazolidinedione (TZD) drugs. Unfortunately, excess adiposity is associated with poor health and glycemic control.

Many AKT inhibitors are known in the art and have been suggested for cancer therapy. (Lindsley, C. W., Curr. Topics in Med. Chem., 10(4):458-477 (2010).)

Thus a need exists for new therapies that are able to improve glycemic control independent of adipogenesis.

SUMMARY OF THE INVENTION

The invention relates to methods of improving glycemic control in an individual, comprising administering to an individual in need thereof a therapeutically effective amount of an Ad36 composition and an AKT1 inhibitor, wherein glycemic control is improved without substantial increase in adipogenesis.

The invention also relates to methods of treating or preventing diabetes in an individual, comprising administering to an individual in need thereof a therapeutically effective amount of an Ad36 composition and an AKT1 inhibitor, wherein the individual's symptoms improve without substantial increase in adipogenesis.

The Ad36 composition can comprise an Adenovirus-36 E4orf1 protein or functional variant thereof, a nucleic acid encoding Adenovirus-36 E4orf1 or functional variant thereof, or an analog or derivative of Adenovirus-36 E4orf1. For example, the amino acid sequence of the Adenovirus-36 E4orf1 protein can be SEQ ID NO:2 or functional variant thereof. In another example, the Ad36 composition can comprise a nucleic acid sequence comprising SEQ ID NO: 1 or functional variant thereof.

In one aspect, a nucleic acid encoding Adenovirus-36 E4orf1 protein is administered to the individual by introducing into the individual a nucleic acid sequence encoding the Adenovirus-36 E4orf1 protein, in a manner permitting expression of the Adenovirus-36 E4orf1 protein. For example, the nucleic acid sequence is introduced by a method selected from the group consisting of electroporation, DEAE Dextran transfection, calcium phosphate transfection, cationic liposome fusion, proptoplast fusion, creation of an in vivo electric field, DNA-coated microprojectile bombardment, injection with recombinant replication-defective viruses, homologous recombination, in vivo gene therapy, ex vivo gene therapy, viral vectors, and naked DNA transfer.

In one aspect, the individual can be a mammal, such as a human.

In one aspect, the AKT1 inhibitor can be 2-Aminothiadiazole (2-ATD).

BRIEF DESCRIPTION OF THE DRAWINGS

FIGS. 7A-C show 3T3-L1 cells that carry an empty vector (pTRE) and do not express E4orf1 in response to doxycycline. FIGS. 7D-F show 3T3-L1 cells that express Ad36 E4orf1 when exposed to doxycycline, treated with 0, 1, or 5 M, respectively, of 2ATD—a specific inhibitor of AKT1 signalling. The results show that 2-ATD blocked adipogenesis and lipid accumulation (staining indicates lipid accumulation).

DETAILED DESCRIPTION

Overview

Figure 1:
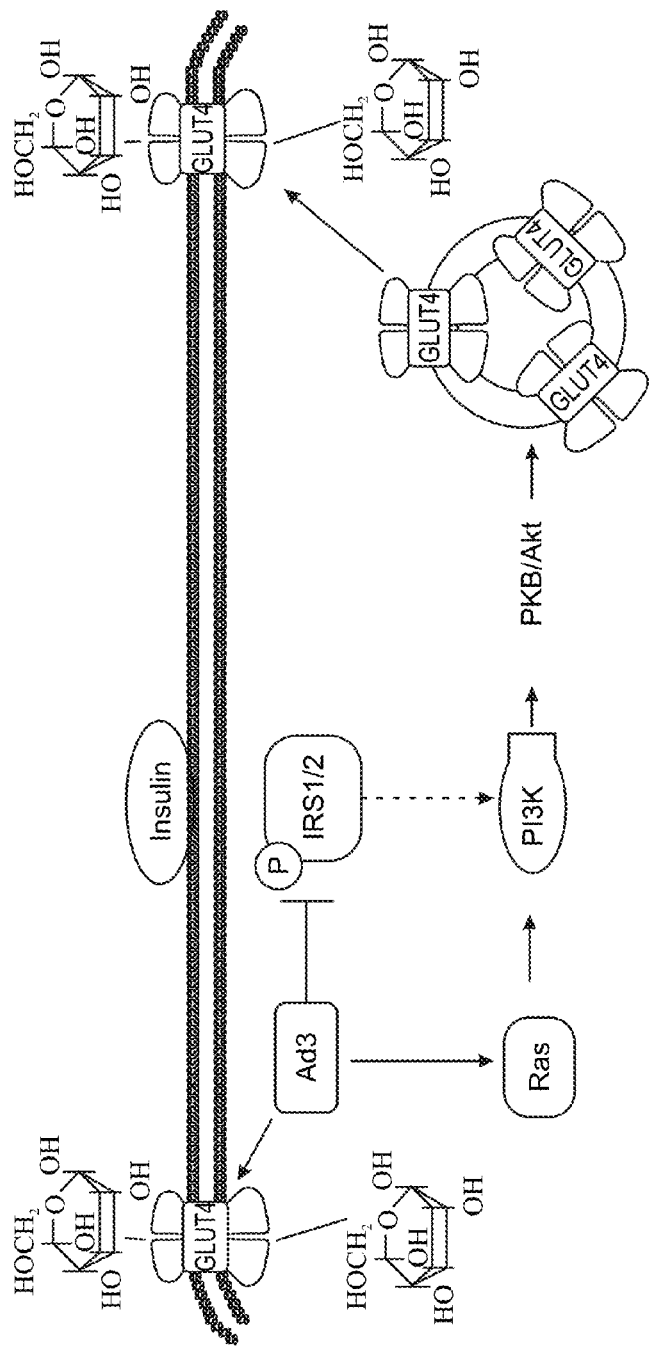
FIG. 1 is a schematic showing the cascade of cell signaling, which involves the activation of phosphatidyl inositol 3-kinase (PI3K) that is initiated upon binding of insulin to its cell surface receptor.

Natural Ad36 infection in humans is associated with better glycemic control, but Ad36 infection also increases adiposity. As described herein, the results of studies using AKT1 inhibitors demonstrate that the Ad36 E4orf1 protein or its analogs or derivatives, in combination with an AKT1 inhibitor enhance glycemic control without inducing adipogenesis.

The inventors have further discovered that an AKT1 inhibitor can block adipogenesis and lipid accumulation in preadipocytes, and reduces the levels of mRNA encoding the adipogenic proteins PPARγ and adiponectin. When AKT1 is inhibited, adipogenesis is blocked, but E4orf1 continues to increase glucose uptake. The Ad36 E4orf1 structure and certain metabolic functions are described in international patent application no. PCT/US2006/045919, published as international patent publication no. WO 2007/064836 on Jun. 7, 2007.

The invention relates to methods for improving glycemic control comprising administering effective amounts of Ad36 E4orf1 or functional variants, analogs or derivatives thereof and an AKT1 inhibitor to an individual in need thereof. Based on the inventors discoveries, hyperglycemia, insulin resistance, prediabetes, diabetes type 1, and diabetes type 2 can be treated or even prevented by administering effective amounts of Ad36 E4orf1 or functional variants, analogs or derivatives thereof and an AKT1 inhibitor to an individual in need thereof.

As used herein, "glycemic control" refers to the ability of the body to keep glucose levels within the normal range. Glycemic control is improved when insulin sensitivity increases. Insulin resistance has the opposite effect on glycemic control.

As used herein, "glucose uptake" refers to the amount of glucose a cell will take in from its surroundings. Generally a higher glucose uptake by muscle cells or fat cells (adipocytes and preadipocytes), is beneficial, as it clears the glucose from circulation and improves hyperglycemia (higher than normal glucose in the blood).

As used herein, an "analog" refers to a small molecule (e.g., less than 1 kDa) that is similar in structure to Ad-36 E4orf1 protein or fragment thereof and that exhibits a qualitatively similar effect on insulin sensitivity as does the Ad-36 E4orf1 protein.

As used herein, a "derivative" refers to a modified Ad-36 E4orf1 protein or functional variant. For example a derivative may be an Ad-36 E4orf1 protein or functional variant that contains one or more D-amino acids or non-naturally occurring amino acids, a pegylated Ad-36 E4orf1, or some other variation on the protein or function variant thereof that exhibits a qualitatively similar effect on insulin sensitivity as does the Ad-36 E4orf1 protein.

As used herein, a "selective AKT1 inhibitor" is an AKT1 inhibitor, that does not substantially inhibit AKT2. For example, a selective AKT inhibitor can have an IC50 for AKT1 that is lower than its IC50 for AKT2 by at least a factor of 10, at least a factor of 25, or at least a factor of 50 (e.g., IC50 for AKT1 inhibitor 4.6 and that for AKT2>250 (see reference—(8)). Preferably, the selective AKT1 inhibitor does not inhibit AKT2 at all.

Therapeutic Methods

The invention provides therapeutic methods for improving glycemic control without increasing adipogenesis. Thus, the invention provides methods for treating or preventing hyperglycemia, insulin resistance, prediabetes or diabetes (type 1 or 2) without increasing adipogenesis.

In one aspect, the invention provides methods for improving glycemic control in an individual (e.g., a mammal, such as a human or other primate). Therapeutically effective amounts of an Ad36 composition and an AKT1 inhibitor are administered to an individual in need thereof to improve glycemic control in the individual.

In one aspect, the invention provides methods for the treatment and prophylaxis of symptoms of hyperglycemia, insulin resistance, prediabetes or diabetes (type 1 or 2). Therapeutically effective amounts of an Ad36 composition and an AKT1 inhibitor are administered to an individual (e.g., a mammal, such as a human or other primate) in need thereof to treat or prevent hyperglycemia, insulin resistance, prediabetes or diabetes (type 1 or 2).

In one aspect, the invention provides methods for treating or preventing insulin resistance. Therapeutically effective amounts of an Ad36 composition and an AKT1 inhibitor are administered is administered to an individual (e.g., a mammal, such as a human or other primate) in need thereof to treat or prevent insulin resistance.

The Ad36 composition that is administered can be an isolated or recombinant Ad36 E4orf1 protein or functional variant thereof. The Ad36 composition can also be an analog or derivative of Ad36 E4orf1 protein. The Ad36 composition that is administered can be an isolated or recombinant nucleic acid that encodes Ad36 E4orf1 protein or functional variant thereof.

The AKT1 inhibitor can be administered before, substantially concurrently with, or subsequent to administration of the Ad36 composition. Preferably, the Ad36 composition and the AKT1 inhibitor are administered so as to provide substantial overlap in their pharmacological activities and provide improved glycemic control without substantially increasing adipogenesis (e.g., no more than 5%, preferably no more than 10% increase in adipogenesis). For example, the AKT1 inhibitor and Ad36 composition can be co-formulated and administered concurrently.

Ad36 Compositions

The Ad36 composition administered in accordance with the invention can have a variety of forms. Preferably, the composition comprises E4orf1 or a functional variant thereof. For example, the Ad36 composition can be the Ad36 virus or an attenuated variant, or an inactivated form of Ad36, such as a heat-killed or bleach-killed Ad36 or a replication deficient recombinant Ad36. The Ad36 composition can comprise an isolated or recombinant Ad36 protein, preferably the E4orf1 protein or a functional variant thereof. The Ad36 composition can comprise a nucleic acid encoding the E4orf1 protein or a functional variant thereof. The Ad36 composition can comprise an analog or derivative of E4orf1 protein, for example a chemical analog or structural analog.

Proteins and Peptides

The Ad36 composition can comprise an isolated or recombinant Ad36 protein, preferably the E4orf1 protein or a functional variant thereof. Proteins or polypeptides referred to herein as "isolated" are proteins or polypeptides purified to a state beyond that in which they exist in infected mammalian cells. Ad36 proteins, including E4orf1 and functional variants thereof, can be produced using well-known methods, such as recombinant expression and purification, chemical synthesis (e.g., synthetic peptides), or by combinations of biological and chemical methods, and recombinant proteins or polypeptides which are isolated. The proteins can be obtained in an isolated state of at least about 50% by weight, preferably at least about 75% by weight, and more preferably, in essentially pure form. Proteins or polypeptides referred to herein as "recombinant" are proteins or polypeptides produced by the expression of recombinant nucleic acids.

As used herein "Ad36 E4orf1" refers to naturally occurring or endogenous E4orf1 proteins from Adenovirus 36, to proteins having an amino acid sequence which is the same as that of a naturally occurring or endogenous corresponding Ad36 E4orf1 (e.g., recombinant and synthetic proteins), and to functional variants of each of the foregoing (e.g., functional fragments and/or mutants produced via mutagenesis and/or recombinant techniques). Accordingly, as defined herein, the term includes mature Ad36 E4orf1, glycosylated or unglycosylated Ad36 E4orf1 proteins, polymorphic or allelic variants, and other isoforms of Ad36 E4orf1 (e.g., produced by alternative splicing or other cellular processes), and functional fragments.

"Functional variants" of Ad36 E4orf1 include functional fragments, and functional mutant proteins. Generally, fragments or portions of Ad36 E4orf1 encompassed by the present invention include those having a deletion (i.e., one or more deletions). For example, 1 to about 75, e.g., 1 to about 50, or 1 to about 25, or 1 to about 10 contiguous or non-contiguous amino acids can be deleted from Ad36 E4orf1. The integrity of the PDZ domain binding motif (the last four amino acids of SEQ ID NO:2) should be maintained, as it is a critical region that should not be altered. Fragments or portions in which only contiguous amino acids have been deleted or in which non-contiguous amino acids have been deleted relative to mature Ad36 E4orf1 are also envisioned. Generally, mutants or derivatives of Ad36 E4orf1, encompassed by the present invention include natural or artificial variants differing by the addition, deletion and/or substitution of one or more contiguous or non-contiguous amino acid residues, or modified polypeptides in which one or more residues is modified, and mutants comprising one or more modified residues. Preferred mutants are natural or artificial variants of Ad36 E4orf1 differing by the addition, deletion and/or substitution of one or more contiguous or non-contiguous amino acid residues.

A "functional fragment or portion" of Ad36 E4orf1 refers to an isolated and/or recombinant protein or oligopeptide which has at least one property, activity and/or function characteristic of Ad36 E4orf1, such as attenuating hepatic steatosis, enhancing glucose disposal, and/or improving glycemic control.

The Ad36 composition can also contain functional fusion proteins that comprise E4orf1 or a functional fragment or variant thereof an a heterologous amino acid sequence.

Generally, the Ad36 E4orf1 or functional variant has an amino acid sequence which is at least about 85% similar, at least about 90% similar, at least about 95% similar, at least about 96% similar, at least about 97% similar, at least about 98% similar, or at least about 99% similar to SEQ ID NO:2 or SEQ ID NO:4 over the length of the variant.

In some embodiments, SEQ ID NO: 1 or SEQ ID NO:3 are used to make purified protein of Ad-36 E4orf1, for example, using currently available recombinant protein production. Amino acid sequence identity can be determined using a suitable amino acid sequence alignment algorithm, such as CLUSTAL W, using the default parameters. (Thompson J. D. et al., Nucleic Acids Res. 22:4673-(1994).)

Nucleic Acids and Vectors

The Ad36 composition can comprise an isolated or recombinant nucleic acid or vector encoding a protein of Ad36, preferably the E4orf1 protein or a functional variant thereof.

An isolated and/or recombinant (including, e.g., essentially pure) nucleic acids which encode an Ad36 E4orf1 protein or functional variant thereof can be administered to cause Ad36 E4orf1 production in situ. Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

Isolated and/or recombinant nucleic acids meeting these criteria comprise nucleic acids having sequences identical to sequences encoding naturally occurring Ad36 E4orf1 and portions thereof, or functional variants of the naturally occurring sequences. Such functional variants include mutants differing by the addition, deletion or substitution of one or more residues as described further herein, and may be encoded by modified nucleic acids in which one or more nucleotides is modified (e.g., DNA or RNA analogs), for example. The sequence can be codon-optimized or codon de-optimized for expression in the individual.

In one aspect, the Ad36 E4orf1 or functional variant is encoded by a nucleic acid that has a nucleic acid sequence which is at least about 85% similar, at least about 90% similar, at least about 95% similar, at least about 96% similar, at least about 97% similar, at least about 98% similar, or at least about 99% similar to SEQ ID NO:1 or SEQ ID NO:3 over the length of the variant. Nucleic acid sequence identity can be determined using a suitable nucleic acid sequence alignment algorithm, such as CLUSTAL W, using the default parameters. (Thompson J. D. et al., Nucleic Acids Res. 22:4673-4680 (1994).)

The nucleic acid can be in the form of DNA, RNA, and can be either single or double stranded. Generally, the nucleic acid is operably linked to expression control sequences such as an origin of replication, a promoter, and an enhancer (see, e.g., Queen, et al., Immunol. Rev. 89:49-68, 1986). A number of suitable vectors for expression of recombinant proteins in desired cells are well-known and conventional in the art. Suitable vectors can contain a number of components, including, but not limited to one or more of the following: an origin of replication; a selectable marker gene; one or more expression control elements, such as a transcriptional control element (e.g., a promoter, an enhancer, a terminator), and/or one or more translation signals; and a signal sequence or leader sequence for targeting to the secretory pathway in a selected host cell. If desired, the vector can include a detectable marker.

In certain embodiments, the expression vectors are used in gene therapy. Expression requires that appropriate regulatory elements be provided in the vectors, such as enhancers/promoters from that drive expression of the genes of interest in host cells. Elements designed to optimize messenger RNA stability and translatability in host cells also are known.

There are a number of ways in which expression vectors may be introduced into cells. In certain embodiments of the invention, the expression construct comprises a virus or engineered construct derived from a viral genome. The ability of certain viruses to enter cells via receptor-mediated endocytosis, to integrate into host cell genome, and express viral genes stably and efficiently have made them attractive candidates for the transfer of foreign genes into mammalian cells (Ridgeway, 1988; Nicolas and Rubinstein, In: Vectors: A survey of molecular cloning vectors and their uses, Rodriguez and Denhardt, eds., Stoneham: Butterworth, pp. 494-513, 1988; Baichwal and Sugden, Baichwal, In: Gene Transfer, Kucherlapati R, ed., New. York, Plenum Press, pp. 117-148, 1986. 1986; Temin, In: Gene Transfer, Kucherlapati, R. ed., New York, Plenum Press, pp. 149-188, 1986). Preferred gene therapy vectors are generally viral vectors.

AKT1 Inhibitors

The Ad36 composition can comprise any AKT1 inhibitor, including 2-ATD; AKT-I-1 (8); 2,3-diphenylquinoxaline (9); regioisomers of 5,6-diphenylpyrazin-2(1H)-ones (pyrazinones) (9); or 8-[4-(1-Aminocyclobutyl)phenyl]-9-phenyl[1,2,4]triazolo[3,4-f]-1,6-naphth-yridin-3(2H)-one (U.S. Pat. No. 7,576,209). Preferably, the AKT1 inhibitor is 2-ATD.

Administering Ad36 Compositions and AKT1 Inhibitors

A variety of routes of administration are possible including, but not necessarily limited to parenteral (e.g., intravenous, intraarterial, intramuscular, subcutaneous injection), oral (e.g., dietary), topical, inhalation (e.g., intrabronchial, intranasal or oral inhalation, intranasal drops), or rectal.

The Adenovirus-36 E4orf1 protein or fragments thereof, or its derivatives, can be administered by introducing into the mammal a nucleic acid sequence encoding the Adenovirus-36 E4orf1 protein, in a manner permitting expression of the Adenovirus-36 E4orf1 protein. In such method, the nucleic acid sequence can be introduced by a method selected from the group consisting of electroporation, DEAE Dextran transfection, calcium phosphate transfection, cationic liposome fusion, proptoplast fusion, creation of an in vivo electric field, DNA-coated microprojectile bombardment, injection with recombinant replication-defective viruses, homologous recombination, in vivo gene therapy, ex vivo gene therapy, viral vectors, naked DNA transfer, and using a nanotechnology delivery system.

Formulation of an Ad36 composition and AKT1 inhibitor to be administered will vary according to the route of administration selected (e.g., solution, emulsion, capsule) and the individual to be treated. An appropriate composition comprising the compound to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, Remington's Pharmaceutical Science, 16th Edition, Mack, Ed. 1980). For inhalation, the compound is solubilized and loaded into a suitable dispenser for administration (e.g., an atomizer, nebulizer or pressurized aerosol dispenser), or formulated as a respirable dry powder. The Ad36 composition and AKT1 inhibitor can be separately formulated or co-formulated.

The Ad36 composition and AKT1 inhibitor can be administered in a single dose or multiple doses. Therapeutically effective amounts are administered. A therapeutically effective amount is an amount sufficient to produce the intended effect under the conditions of administration. For example, an amount of Ad36 composition that is sufficient to increase fat oxidation, increase transport of fat out of the liver, to lower Glut2 abundance in the liver, to reduce G6Pase in the liver, to enhance adiponectin, and/or Glut4, to improve glycemic control and/or to improve liver function can be administered. An amount of AKT1 inhibitor that is sufficient to inhibit adipogenisis, reduce mRNA levels of PPARγ and/or adiponectin function can be administered. The appropriate dosages can be determined by a clinician of ordinary skill using methods known in the art, which take into consideration the individual's age, sensitivity to drugs, tolerance to drugs, severity of disease and overall well-being, as well as other factors. Suitable dosages can be from about 0.1-about 10.0 mg/kg body weight per treatment.

The entire teachings of all documents cited herein are hereby incorporated herein by reference.

Ad36 E4orf1 Sequences

Ad-36 E4orf1 DNA sequence
(SEQ ID NO. 1)
ATGGCTGAATCTCTGTATGCTTTCATAGATAGCCCTGGAGGGATCGCTCC

CGTCCAGGAAGGGGCTAGCAATAGATATATCTTCTTTTGCCCCGAATCTT

TCCACATTCCTCCGCATGGGTGATATTGCTTCACCTCAGAGTGAGCGTG

CTGGTTCCTACTGGATATCAGGGCAGATTTATGGCCTTGAATGACTACCA

-continued

Ad36 E4orf1 Sequences

TGCCAGGGGCATACTAACCCAGTCCGATGTGATATTTGCCGGGAGAAGAC

ATGATCTCTCTGTGCTGCTCTTTAACCACACGGACCGATTTTTGTATGTC

CGCGAGGGCCACCCAGTGGGAACCCTGCTGCTGGAGAGAGT GATTTTTC

CTTCAGTGAGAATAGCCACCCTGGTTTAG

Ad-36 E4orf1 Protein translation (SEQ ID NO. 2)
MAESLYAFIDSPGGIAPVQEGASNRYIFFCPESFHIPPHGVILLHLRVSV

LVPTGYQGRFMALNDYHARGILTQSDVIFAGRRHDLSVLLFNHTDRFLYV

REGHPVGTLLLERVIFPSVRIATLV

EXEMPLIFICATION

The results of the studies disclosed herein revealed that there is a link between Ad36 infection in humans and better glycemic control. The results also demonstrate that the Ad36 E4orf1 protein when combined with an AKT1 inhibitor improves glucose disposal, without increasing adipogenesis. Thus, these studies disclosed herein show that Ad36, Ad36 E4orf1, and functional variants combined with an AKT1 inhibitor can be used to treat or prevent hyperglycemia, insulin resistance, prediabetes, diabetes (type 1 or 2), and improve glycemic control without increasing adipogenesis.

The interaction of Ad36 with AKT was investigated. AKT1, AKT2 and AKT3 are isoforms of this enzyme. Activation of AKT1 lead to an up-regulation of PPARγ and consequential adipogenesis, whereas, the activation of AKT2 lead to increased glucose uptake. AKT3 is primarily expressed in the brain.

Figure 5A:
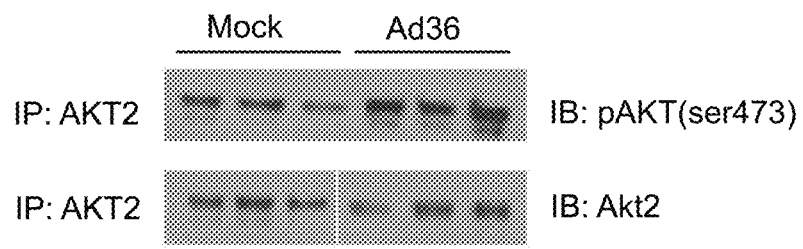
FIG. 5 (A) is a Western blot showing the levels of total and phosphorylated AKT2 proteins isolated from differentiated 3T3L1 adipocytes; (B) is a graph showing Ad36 significantly increased AKT2 activation compared with mock (*p<0.05).
Figure 5B:
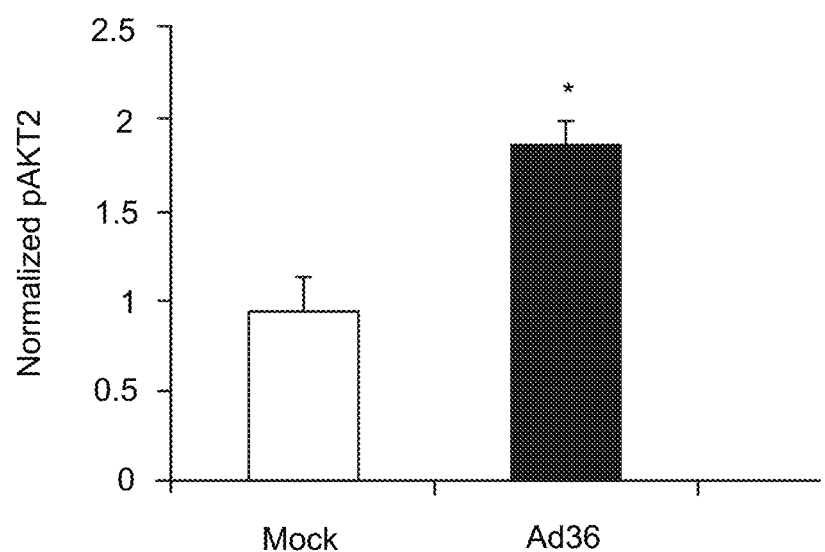
Figure 6:
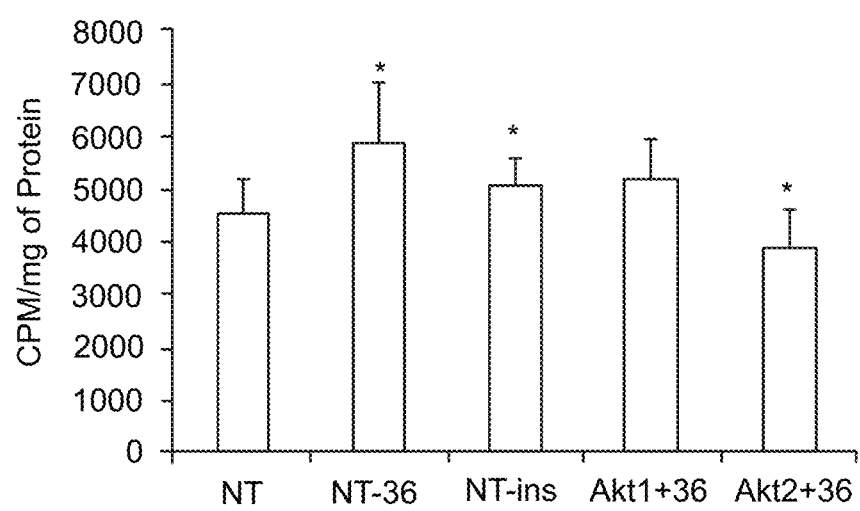
FIG. 6 is a graph showing glucose uptake after AKT knock down with siRNA. The data shows that AKT2, but not AKT1, is required for Ad36 to enhance cellular glucose uptake.
Figure 7:
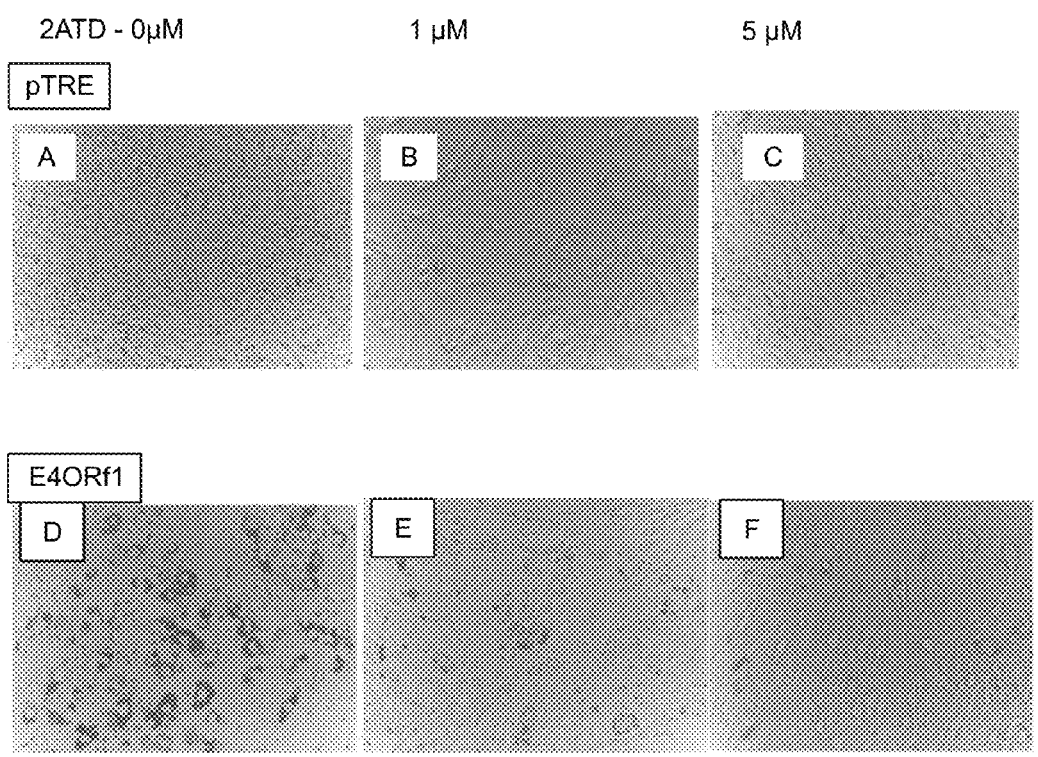
FIG. 7A-F are photomicrographs of 3T3-L1 cells.

Ad36 infection up-regulated the activation of AKT1 and AKT2 in mice (FIGS. 2 & 3). Chow-fed mice infected with Ad36 increased adiposity in response to infection and yet, improved their glycemic control This is reflected in greater activation of AKT1 and AKT2 in Ad36 infected chow fed mice. On the other hand, high-fat fed mice were already fat and did not increase adiposity further in response to Ad36 infection. They did however, improve glycemic control in response to Ad36 infection. This is reflected in greater AKT2 activation (but no difference in AKT1 activation) in these mice compared to uninfected controls. It was also discovered that Ad36 significantly increased the activation of AKT1 & AKT2 in differentiating preadipocytes (3T3-L1 cells), and increased AKT2 activation in differentiated 3T3-L1 adipocytes (FIGS. 4 & 5). 3T3-L1 cells were used as a model to study AKT enzymes further as described herein. Moreover, by selectively knocking down AKT1 or AKT2 using siRNA, it was shown that AKT2, but not AKT1, is required for Ad36 to enhance cellular glucose uptake (FIG. 6).

Example 1

Ad36 Activates AKT2 in High-Fat (HF)-Fed Mice

Figure 2A:
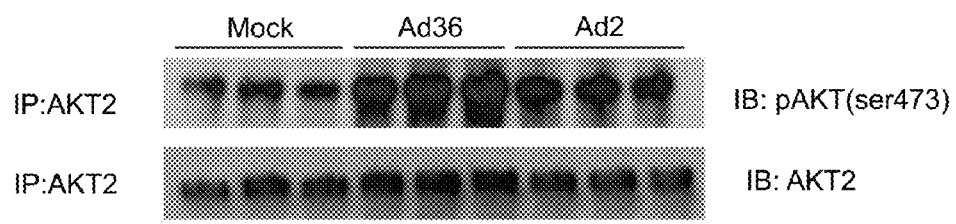
FIG. 2 (A) is a Western blot showing the levels of total and phosphorylated (activated) AKT2 protein isolated from adipose tissue of HF-fed mice killed 20 weeks after infection with adenoviruses Ad36 or Ad2 (a negative control virus); (B) is a graph showing Ad36 infected mice, but not Ad2 infected mice, had greater AKT2 activation (as indicated by greater phosphorylation) compared with mock (*p<0.05).
Figure 2B:
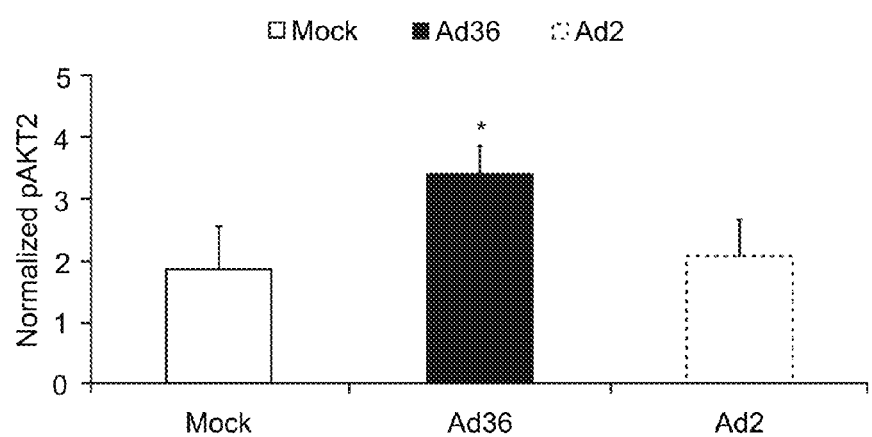

Proteins were isolated from adipose tissue of HF-fed mice killed 20 weeks after infection with adenoviruses Ad36 or Ad2 (a negative control virus) or mock infection (n=3 mice/group). AKT2 protein was isolated with isoform-specific AKT antibodies by immunoprecipitation. The levels of total and phosphorylated AKT2 were determined by western blotting (FIG. 2A). Densitometry analysis was used to quantitate protein abundance and compared to Mean±SE. Ad36 infected mice, but not Ad2 infected group, had greater AKT2 activation (as indicated by greater phosphorylation) compared with mock (*$p<0.05$) (FIG. 2B).

Example 2

Ad36 Activates AKT1 and AKT2 in Chow Fed Mice

Figure 3A:
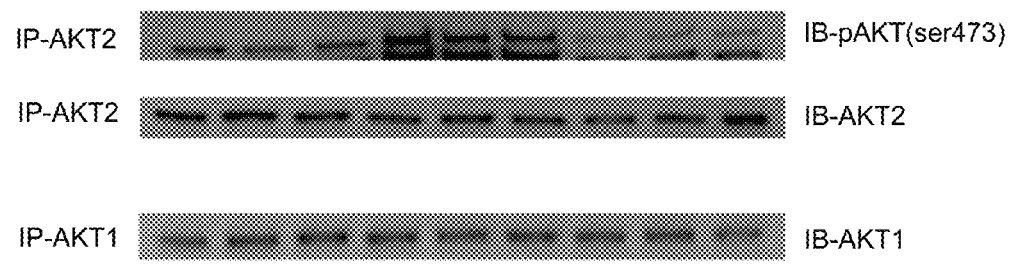
FIG. 3 (A) is a Western blot showing the levels of total and phosphorylated AKT1 and AKT2 proteins isolated from adipose tissue of chow-fed mice killed 12 weeks after infection with Ad36 or Ad2 or mock infection; (B and C) are graphs showing Ad36 infected mice, but not Ad2 infected mice, had greater AKT1 and AKT2 activation, respectively, (as indicated by greater phosphorylation) compared with mock (*p<0.05 or better).
Figure 3B:
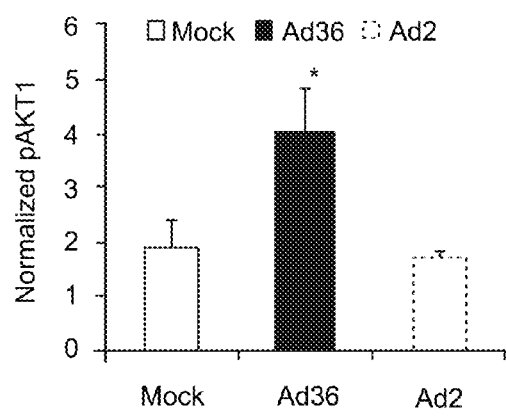
Figure 3C:
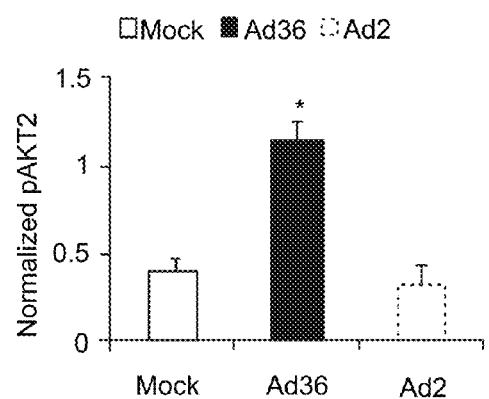

Proteins were isolated from adipose tissue of chow-fed mice killed 12 weeks after infection with Ad36 or Ad2 or mock infection (n=3 mice/group). AKT1 and AKT2 proteins were isolated with isoform-specific AKT antibodies by immunoprecipitation. The levels of total and phosphorylated AKT1 and AKT2 were determined by western blotting (FIG. 3A). Densitometry analysis was used to quantitate protein abundance and compare Mean±SE. Ad36 infected mice, but not Ad2 infected mice, had greater AKT1 and AKT2 activation (as indicated by greater phosphorylation) compared with mock (*$p<0.05$ or better) (FIGS. 3B and 3C).

Example 3

Ad36 Activates AKT1 and AKT2 in 3T3L1 Cells During Differentiation

Figure 4A:
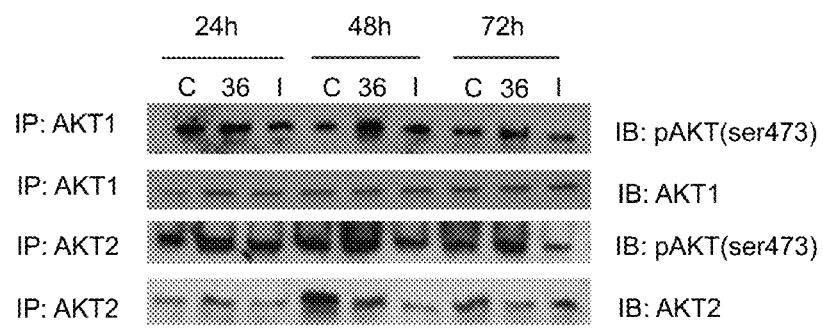
FIG. 4 (A) is a Western blot showing the levels of total and phosphorylated AKT1 and AKT2 proteins from 3T3L1 cells that were induced to differentiate in to adipocytes, (B and C) are graphs showing Ad36 significantly induced increased in AKT1 and AKT2 activation, respectively, compared with mock (*p<0.05 or better). The effect of Ad36 on AKT was similar to or better than that of insulin.
Figure 4B:
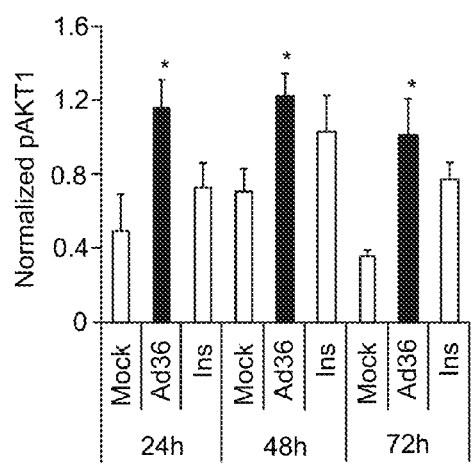
Figure 4C:
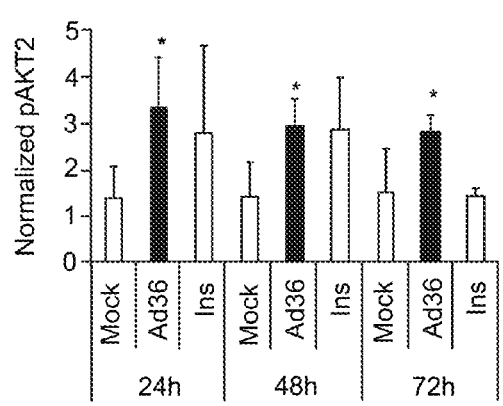

3T3L1 preadipocytes were Ad36 or mock infected (n=3/group). 3T3L1 cells were induced to differentiate into adipocytes. Proteins were harvested 24, 48 and 72 hours after infection. AKT1 and AKT2 proteins were isolated with isoform-specific AKT antibodies by immunoprecipitation. The levels of total and phosphorylated AKT1 and AKT2 were determined by western blotting (FIG. 4A). Densitometry analysis was used to quantitate protein abundance and compare Mean±SE. Ad36 significantly induced increase in AKT1 and AKT2 activation compared with mock (*$p<0.05$ or better) (FIGS. 4B and 4C). The effect of Ad36 on AKT was similar to or better than that of insulin.

Example 4

Ad36 Activates AKT2 in 3T3L1 in Adipocytes

Differentiated 3T3L1 adipocytes were Ad36 or mock infected (n=3/group). Proteins were harvested 24 hours post infection. AKT2 protein was isolated with isoform-specific AKT antibodies by immunoprecipitation. The levels of total and phosphorylated AKT2 were determined by western blotting (FIG. 5A). Densitometry analysis was used to quantitate protein abundance and compare Mean±SE. Ad36 significantly increased AKT2 activation compared with mock (*$p<0.05$) (FIG. 5B).

Example 5

Glucose Uptake after AKT Knock Down with siRNA 2-deoxy glucose (2DG) uptake was determined under basal and insulin stimulated conditions 3 days post transfection, in 3T3-L1 preadipocytes. NT: cells transfected with non-targeting siRNA. Akt1 and Akt2: cells transfected with Akt1 and Akt2 siRNA. NT+Ad36: cells transfected with non-targeting siRNA and infected with Ad36. Akt1+36 and Akt2+36: cells transfected with Akt1 and Akt2 siRNA separately and infected with Ad36. Nt-Ins: cells transfected with non-targeting siRNA+ insulin. Akt1+Ins and Akt2+Ins: cells transfected with Akt1 and Akt2 siRNA+ insulin. As expected, Ad36 significantly increased glucose uptake. The results show that knockdown of AKT2, but not of AKT1, decreased Ad36 induced glucose uptake (*p<0.05) (FIG. 6).

Example 6

Chemical Inhibition of AKT1 Using 2-ATD in Inducible E4orf1 Stable Cell Line

3T3-L1 cells that express Ad36 E4orf1 when exposed to doxycycline (10) were generated. Cells that carry an empty vector (pTRE) and do not express E4orf1 in response to doxyclycline were used as controls. Confluent E4orf1 and pTRE cells were exposed to adipogenic media to induce differentiation. In addition the cells were treated with 0, 1 or 5 M of 2ATD—a specific inhibitor of AKT1 signalling. This media was refreshed every two days for up to nine days. Adipogenic differentiation was verified by oil red O staining (FIGS. 7A-F).

Example 7

Chemical Inhibition of AKT1 Using 2-ATD in Inducible E4orf1 Stable Cell Line

Figure 8A:
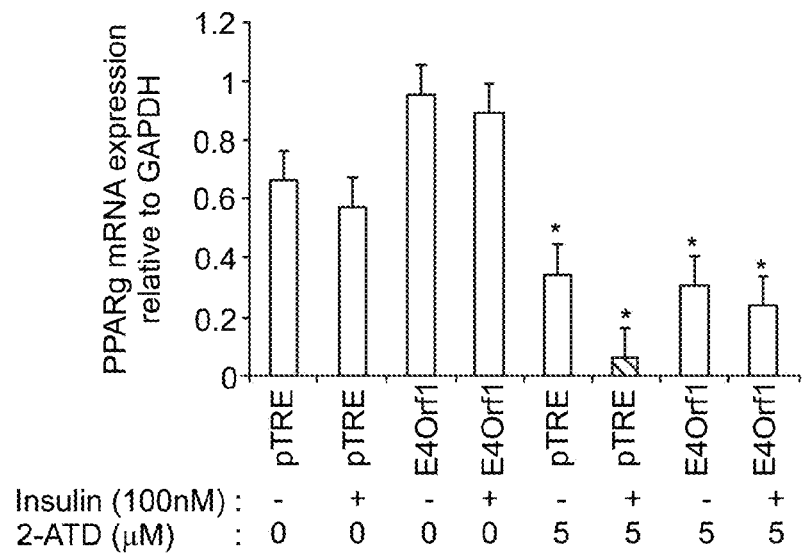
FIG. 8 (A) is a graph showing the effect of chemical inhibition of AKT1 using 2-ATD on PPARγ expression in an inducible E4orf1 stable cell line; (B) is a graph showing the effect of chemical inhibition of AKT1 using 2-ATD on adiponetin expression. FIGS. A and B show a down regulation of mRNA expression of adipogenic genes, PPARγ and adiponectin, when exposed to 2-ATD.
Figure 8B:
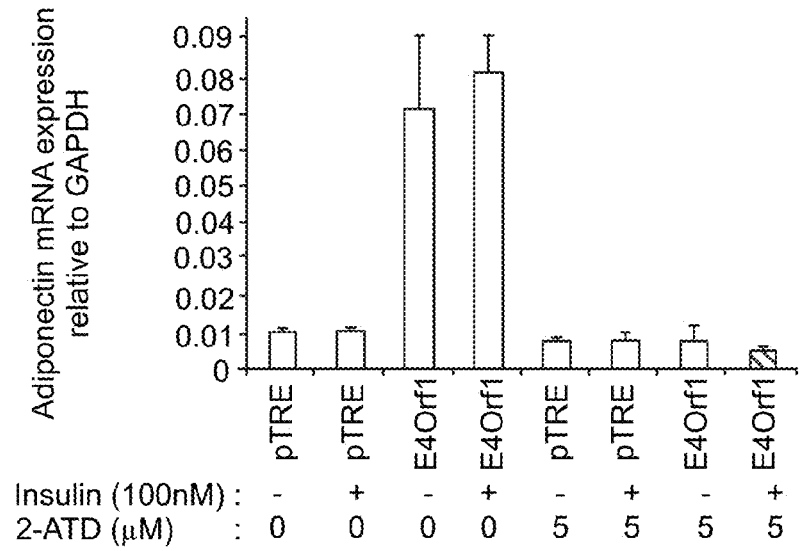

Confluent E4orf1 and pTRE cells were exposed to adipogenic media to induce differentiation. In addition the cells were treated with 0 or 5 µM of 2ATD—a specific inhibitor of AKT1 signalling. This media was refreshed every two days for up to nine days. Basal and insulin stimulated 2DG uptake was determined 24 hours post induction in the presence of 1000 ng/ml of doxycycline expression of PPARγ and adiponectin—markers of adipogenesis, by qRT-PCR. As expected, E4orf1 expression significantly increased the expression of PPARγ and adiponectin. 2-ATD treatment significantly reduced PPARγ expression in pTRE as well as E4orf1 expressing cells (FIG. 8A) and adiponectin expression in E4orf1 expressing cells (FIG. 8B).

Example 8

Basal and Insulin Stimulated Glucose Uptake in Presence of 2-ATD

Figure 9:
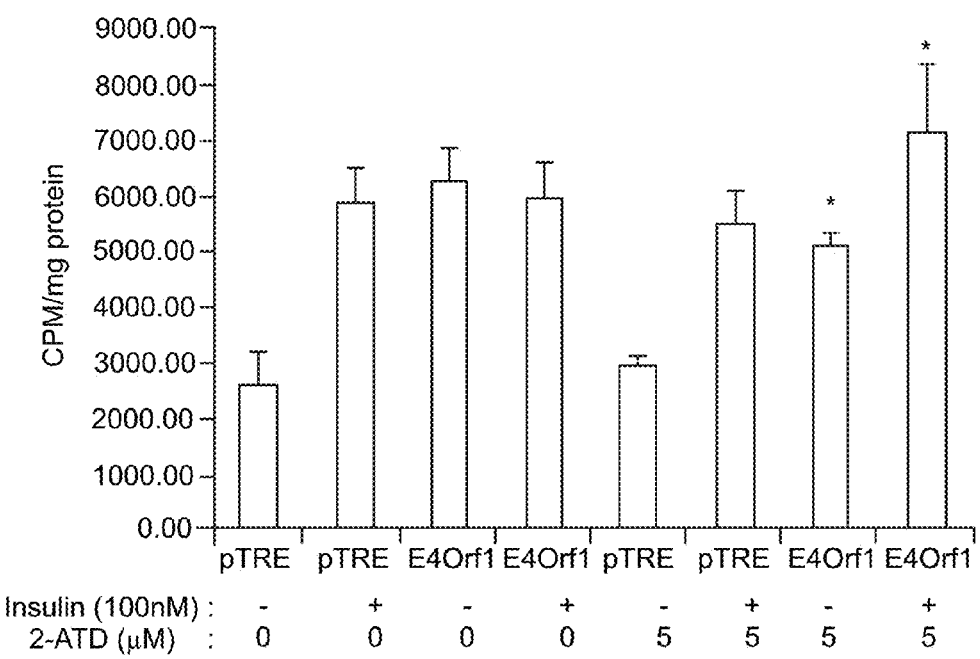
FIG. 9 is a graph showing basal and insulin stimulated glucose uptake in the presence of 2-ATD. The graph shows that E4orf1 expression continued to increase glucose uptake, when exposed to 2-ATD.

E4orf1 and pTRE inducible stable cells were exposed to adipogenic media to induce differentiation and treated with 0 or 5 µM of 2-ATD. Basal and insulin stimulated 2DG was determined 24 hours after exposure to doxycycline (1000 ng/ml), in presence or absence of insulin (*p<0.05). E4orf1 expression increased glucose uptake compared to that in pTRE. Despite 2-ATD treatment, E4orf1 expressing cells continued to show significantly greater glucose uptake (FIG. 9).

Example 9

ATD Inhibits PPARγ Protein Abundance

Figure 10:
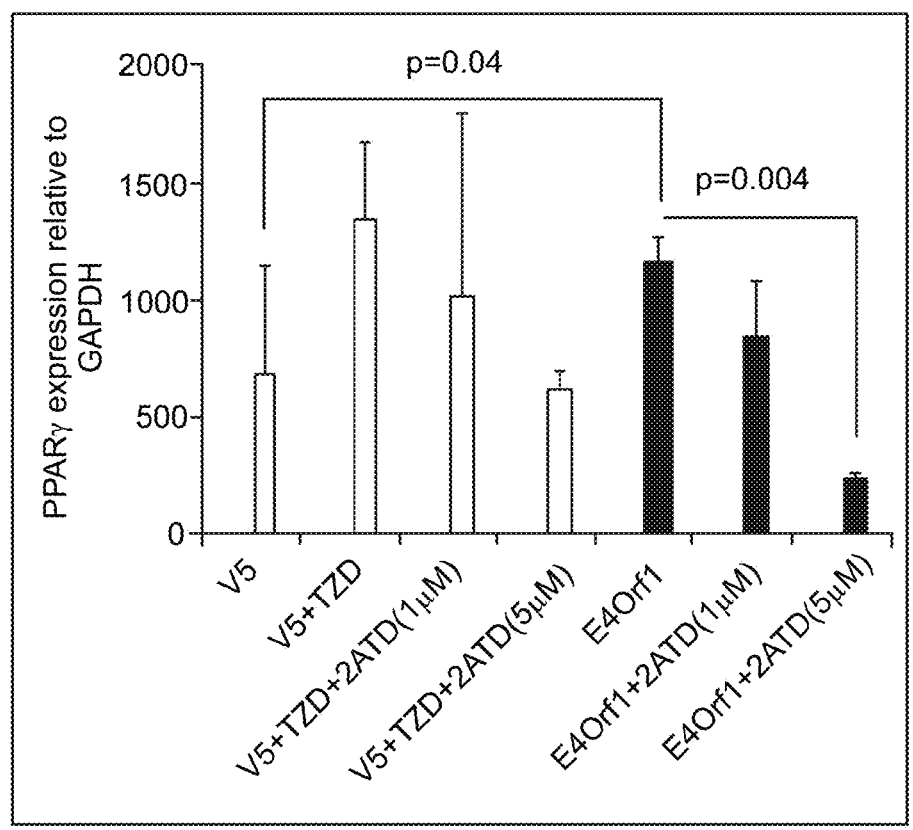
FIG. 10 is a graph showing ATD inhibits PPARγ protein abundance. 3T3-L1 adipocytes were transfected with a null vector (V5), and exposed to 10 μM TZD, or transfected with a plasmid expressing E4orf1 protein. Both groups were exposed to 0, 1 or 5 LM ATD.

3T3-L1 adipocytes were transfected with a null vector and exposed to 10 µM TZD, or transfected with a plasmid expressing E4orf1 protein. Both groups were exposed to 0, 1 or 5 µM ATD. ATD reduced PPARγ protein abundance. Increasing concentration of ATD significantly reduced glucose uptake in the presence of TZD, but not when transfected with E4orf1 (FIG. 10). The glucose uptake in adipocytes was PPARγ-dependent in the presence of TZD, but not when induced by E4orf1. Thus, by down-regulating AKT-1 signaling E4orf1 can be used to enhance glucose uptake by adipocytes, without further increasing lipid accumulation. These data show a way to harness the anti-diabetic potential of E4orf1 without its adipogenic effect.

REFERENCES

1. Lindsley C W. The Akt/PKB family of protein kinases: a review of small molecule inhibitors and progress towards target validation: a 2009 update. *Curr Top Med Chem* 2010; 10: 458-477.
2. Cho H, Thorvaldsen J L, Chu Q, Feng F, Birnbaum M J. Akt1/PKBalpha is required for normal growth but dispensable for maintenance of glucose homeostasis in mice. *J Biol Chem* 2001; 276: 38349-38352.
3. Cho H, Mu J, Kim J K, Thorvaldsen J L, Chu Q, Crenshaw E B, 3rd, et al. Insulin resistance and a diabetes mellitus-like syndrome in mice lacking the protein kinase Akt2 (PKB beta). *Science* 2001; 292: 1728-1731.
4. Garofalo R S, Orena S J, Rafidi K, Torchia A J, Stock J L, Hildebrandt A L, et al. Severe diabetes, age-dependent loss of adipose tissue, and mild growth deficiency in mice lacking Akt2/PKB beta. *J Clin Invest* 2003; 112: 197-208.
5. Hill M M, Clark S F, Tucker D F, Birnbaum M J, James D E, Macaulay S L. A role for protein kinase Bbeta/Akt2 in insulin-stimulated GLUT4 translocation in adipocytes. *Mol Cell Biol* 1999; 19: 7771-7781.
6. Easton R M, Cho H, Roovers K, Shineman D W, Mizrahi M, Forman M S. et al. Role for Akt3/protein kinase Bgamma in attainment of normal brain size. *Mol Cell Biol* 2005; 25: 1869-1878.
7. Luo J, Manning B D, Cantley L C. Targeting the PI3K-Akt pathway in human cancer: rationale and promise. *Cancer Cell* 2003; 4: 257-262.
8. Barnett S F, Defeo-Jones D, Fu S, Hancock P J. Haskell K M, Jones R E, et al. Identification and characterization of pleckstrin-homology-domain-dependent and isoenzyme-specific Akt inhibitors. *Biochem J* 2005; 385: 399-408.
9. Lindsley C W, Zhao Z, Leister W H, Robinson R G, Barnett S F, Defeo-Jones D, et al. Allosteric Akt (PKB) inhibitors: discovery and SAR of isozyme selective inhibitors. *Bioorg Med Chem Lett* 2005; 15: 761-764.

What is claimed is:

1. A method of improving glycemic control in an individual, comprising administering to the individual in need thereof a therapeutically effective amount of an Adenovirus-36 (Ad36) E4orf1 protein or a functional variant thereof and a selective AKT1 inhibitor, wherein glycemic control is improved without substantial increase in adipogenesis.

2. A method of increasing insulin sensitivity in an individual, comprising administering to the individual in need thereof a therapeutically effective amount of an Adenovirus-36 (Ad36) E4orf1 protein or a functional variant thereof and a selective AKT1 inhibitor, wherein insulin sensitivity is increased without substantial increase in adipogenesis.

3. A method of treating hyperglycemia or insulin resistance in the individual, comprising administering to an individual in need thereof a therapeutically effective amount of an Adenovirus-36 (Ad36) E4orf1 protein or a functional variant thereof and a selective AKT1 inhibitor, wherein the individual's symptoms improve without substantial increase in adipogenesis.

4. The method of claim 1, wherein the amino acid sequence of the Adenovirus-36 E4orf1 protein is SEQ ID NO:2 or a functional variant thereof.

5. The method of claim 1, wherein said individual is a human.

6. The method of claim 1, wherein said AKT1 inhibitor is 2-Aminothiadiazole (2-ATD).

* * * * *